(12) United States Patent
Sting

(10) Patent No.: US 6,222,037 B1
(45) Date of Patent: Apr. 24, 2001

(54) PROCESS FOR PREPARATION OF SULFONYLUREA SALTS

(75) Inventor: Andrea Rolf Sting, Gipf-Oberfrick (CH)

(73) Assignee: Syngenta Crop Protection, Inc., Greensboro ( * ) Notice: Subject to any disclaimer, the term of this patent is extended or adjusted under 35 U.S.C. 154(b) by 0 days.

(21) Appl. No.: 09/139,996

(22) Filed: Aug. 25, 1998

(30) Foreign Application Priority Data

Sep. 5, 1997 (CH) .................................................. 2084/97

(51) Int. Cl.$^7$ ................................................. C07D 239/52
(52) U.S. Cl. ............................................................. 544/320
(58) Field of Search ............................................. 544/320

(56) References Cited

U.S. PATENT DOCUMENTS

| | | | |
|---|---|---|---|
| 4,127,405 | | 11/1978 | Levitt . |
| 4,534,790 | * | 8/1985 | Wolf ..................... 544/207 |
| 4,579,583 | | 6/1993 | Föry et al. ............. 504/178 |
| 4,789,393 | * | 12/1988 | Hanagar ................. 544/320 |
| 5,102,444 | * | 4/1992 | Liang ..................... 544/320 |
| 5,221,315 | | 6/1993 | Föry et al. ............. 504/178 |
| 5,403,814 | * | 4/1995 | Fory ....................... 544/320 |
| 5,457,084 | * | 10/1995 | Sakashita ............... 544/320 |
| 5,494,886 | * | 2/1996 | Kehne et al. .......... 544/320 |
| 5,532,203 | * | 7/1996 | Fory et al. ............. 544/320 |
| 5,886,176 | * | 3/1999 | Muller ................... 544/219 |

FOREIGN PATENT DOCUMENTS

| | | |
|---|---|---|
| 33846/93 | 9/1993 | (AU) . |
| 36 09 700 | 9/1987 | (DE) . |
| 44 40 355 | 5/1996 | (DE) . |
| 0 232 067 | 8/1987 | (EP) . |
| 0 521 500 | 1/1993 | (EP) . |
| 559044 | 9/1993 | (EP) . |
| WO 92/16522 | 10/1992 | (WO) . |
| WO 96/15119 | 5/1996 | (WO) . |

OTHER PUBLICATIONS

Cram ø Hammond, "Organic Chemistry" pp. 565–567 McGraw–Hill Book Co, New York (2nd Ed 1964).*
DAUS "Intellectual Property Jour " vol. 12, No. 2, Sep. 1998, pp. 333–354.*
Derwent Abstracts, 93–002046 [01] (EP 521 500) Abstract Jul. 7, 1993.
Derwent Abstract 87–272017/19839 (of DE 36 09 700).
Derwent Abstract 96–240123/199625 (of DE 44 40 355).
J. Agric. Food Chem., vol. 41, No. 12, pp. 2404–2410, 1993.
J. Med Chem., vol. 16, No. 12, pp. 1340–1346, 1973.
Bull. Soc. Chim. Fr., 10, pp. 3600–3603, 1971.
Chemical Abstract 76:45902 (of Bull. Soc. Chem. Fr., 10, pp. 3600–3603, 1971.
J. Prakt. Chem., Band 331, No. 1, pp. 121–128, 1989.

\* cited by examiner

*Primary Examiner*—John M. Ford
(74) *Attorney, Agent, or Firm*—William A. Teoli, Jr.

(57) ABSTRACT

A process for the preparation of a compound of formula I

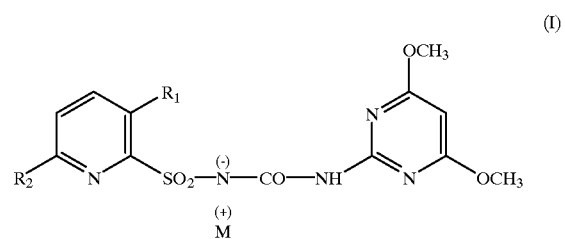

wherein $R_1$ is selected from the group consisting of $-CO_2CH_3$, $-CON(CH_3)_2$, $-OCH_2CF_3$, $-N(CH_3)COCH_3$, $-N(CH_3)SO_2CH_3$, $-CF_3$, and $-SO_2C_2H_5$;

$R_2$ is selected from the group consisting of hydrogen and $-CF_3$; and

M is selected from the group consisting of sodium and potassium;

comprising: reacting a compound of formula IV

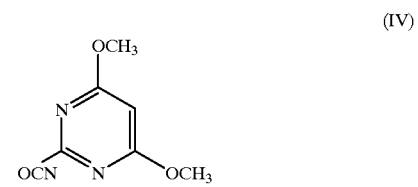

in an aprotic, organic solvent with a compound of formula V

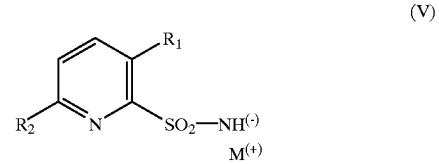

wherein $R_1$, $R_2$, and M are as defined above.

4 Claims, No Drawings

PROCESS FOR PREPARATION OF SULFONYLUREA SALTS

The present invention relates to a process for the preparation of potassium and sodium salts of N-pyridylsulfonyl-N'-pyrimidinylureas.

It is known how to prepare N-pyridylsulfonyl-N'-pyrimidinylureas in a manner such that a pyridylsulfonamide is reacted with a pyrimidinyl isocyanate in the presence of a base. Such reactions are described, for example, in EP-A-0 232 067, EP-A-0 459 949 or EP-A-0 540 697. The corresponding sulfonylurea salts are obtained by reacting the sulfonylureas thus prepared in a second reaction step with suitable salt-forming substances. Such salt-forming substances are bases which are able to abstract the acidic hydrogen atom in the $SO_2$—NH—CO group, for example hydrides, hydroxides, alcoholates, hydrogen carbonates, and carbonates of alkali metals and alkaline earth metals. Such reactions are described, for example, in EP-A-0 521 500. This two-step synthesis, however, has a major disadvantage. The sulfonylureas thus obtained generally possess only a weak crystalline structure and can therefore only be filtered off from the reaction mixture with difficulty and in very insufficient quantities. This especially hinders the economic manufacture of such compounds on a large scale. Moreover, the yields obtained by means of the known processes are as a rule unsatisfactory.

It is therefore the purpose of the present invention to make available a process for the preparation of N-pyridylsulfonyl-N'-pyrimidinylurea sodium and potassium salts which is characterised by a simple reaction procedure and which avoids the disadvantages of the known processes.

It has now been found that N-pyridylsulfonyl-N'-pyrimidinylurea salts can be prepared in a simple manner and with high yields by either reacting a pyridylsulfonamide salt with a pyrimidinyl isocyanate or a pyridylsulfochloride with a pyrimidinylurea salt.

According to the invention, it is therefore proposed that compounds of formula I

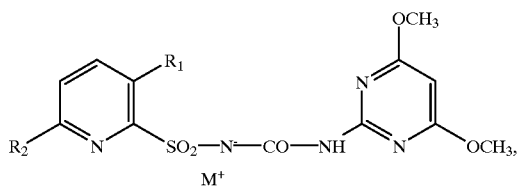

wherein $R_1$ is $CO_2CH_3$, $CON(CH_3)_2$, $OCH_2CF_3$, $N(CH_3)COCH_3$, $N(CH_3)SO_2CH_3$, $CF_3$ or $SO_2C_2H_5$; $R_2$ is hydrogen or $CF_3$; and M is sodium or potassium, are prepared in a manner such that a compound of formula IV

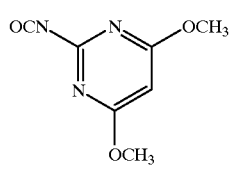

is reacted in an aprotic, organic solvent either with a compound of formula V

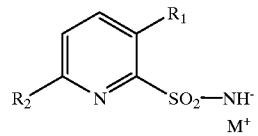

wherein $R_1$, $R_2$ and M are as defined under formula I, or is reacted with $NH_3$ in an aprotic, organic solvent to form a compound of formula III

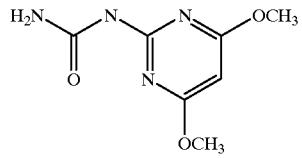

reacting this with a hydride, hydroxide, alcoholate, hydrogen carbonate or carbonate of sodium or potassium in an aprotic, organic solvent to form a compound of formula II

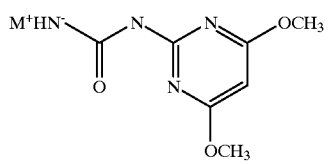

wherein M is as defined under formula I, and then reacting this with a compound of formula VI

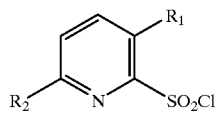

wherein $R_1$ and $R_2$ are as defined under formula I.

Aprotic, organic solvents suitable for reacting a compound of formula IV with a compound of formula V are, for example, ethyl acetate, acetonitrile, dimethylsulfoxide, dimethylformamide, dimethylacetamide, N-methyl-2-pyrrolidone, acetone, butanone, halogenated solvents such as dichloromethane, trichloromethane or trichlorethane, ethers such as tetrahydrofuran, diethylether, 1,2-dimethoxyethane, dioxane, methyl-tert-butylether, and also aromatic solvents such as chlorobenzene, toluene and xylene. Dioxane and tetrahydrofuran are especially preferred. The reaction of a compound of formula IV with a compound of formula V is carried out at temperatures of from $-20°$ C. to $180°$ C., a temperature range of from 30 to $80°$ C. being preferred. The compounds of formulae IV and V can be used in equivalent stoichiometric quantities, although a slight excess of isocyanate may be of advantage.

Aprotic, organic solvents suitable for the transformation of a compound of formula IV to a compound of formula III are, for example, ethyl acetate, acetonitrile, dimethylsulfoxide, dimethylformamide, dimethylacetamide, N-methyl-2-pyrrolidone, acetone, butanone, halogenated solvents such as dichloromethane, trichloromethane or trichlorethane, ethers such as tetrahydrofuran, diethylether, 1,2-dimethoxyethane, dioxane, methyl-tert-butylether, and also aromatic solvents such as chlorobenzene, toluene and xylene. Dioxane and tetrahydrofuran are especially preferred. The reaction is carried out at temperatures of −20° C. to 180° C., a temperature range of 0–80° C. being preferred. The stochiometric ratio of the compound of formula IV to the $NH_3$ used is 1:1 to 1:3, preferably 1:1.5.

Aprotic, organic solvents suitable for converting a compound of formula III to a compound of formula II are, for example, ethyl acetate, acetonitrile, dimethylsulfoxide, dimethylformamide, dimethylacetamide, N-methyl-2-pyrrolidone, acetone, butanone, halogenated solvents such as dichloromethane, trichloromethane or trichlorethane, ethers such as tetrahydrofuran, diethylether, 1,2-dimethoxyethane, dioxane, methyl-tert-butylether, and in the broader sense also aromatic solvents such as chlorobenzene, toluene and xylene, as well as alcohols such as $C_1$–$C_5$ alcohols, typically methanol or ethanol. Tetrahydrofuran is especially preferred.

Aprotic, organic solvents suitable for reacting a compound of formula II with a compound of formula VI are, for example, ethyl acetate, acetonitrile, dimethylsulfoxide, dimethylformamide, dimethylacetamide, N-methyl-2-pyrrolidone, acetone, butanone, halogenated solvents such as dichloromethane, trichloromethane or trichlorethane, ethers such as tetrahydrofuran, diethylether, 1,2-dimethoxyethane, dioxane, methyl-tert-butylether, and in the broader sense also aromatic solvents such as chlorobenzene, toluene and xylene. Tetrahydrofuran is especially preferred. The reaction is carried out at temperatures of −20° C. to 180° C., a temperature range of 0–40° C. being preferred. The stoichiometric ratio between the compound of formula III, the base, and the compound of formula VI is 1:2:1 to 1:3:2, preferably 1:2:1.1. Bases suitable for salt formation are, for example, the hydrides, carbonates, hydrogen carbonates and alcoholates of sodium and potassium, preferably the hydrides and alcoholates, such as sodium hydride, potassium hydride, sodium methylate, potassium methylate or potassium ethylate, special preference being for sodium hydride and sodium methylate.

In the process according to the invention, a compound of formula IV

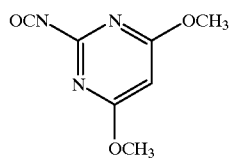

(IV)

is preferably reacted in an aprotic, organic solvent with a compound of formula V

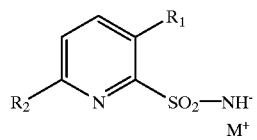

(V)

wherein $R_1$, $R_2$ and M are as defined under formula I. Special attention is drawn to the surprisingly high yield with this variant.

Especially preferred are those compounds of formula I which are prepared using the process according to the invention, wherein $R_1OCH_2CF_3$ and $R_2$ are hydrogen. In a further group of preferred compounds of formula I, M is sodium.

In a preferred variant of the process according to the invention, 3-(2-trifluoroethoxy)pyridin-2-ylsulfonamide sodium salt is reacted at a temperature of 30 to 80° C. in dioxane or tetrahydrofurane with 4,6-dimethoxypyrimidin-2-isocyanate.

The intermediate products of formula II

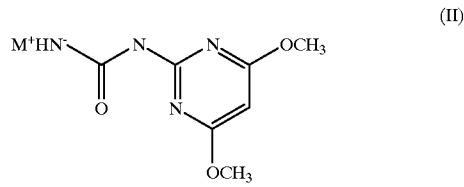

(II)

wherein M is as defined under formula I, and the intermediate product of formula III

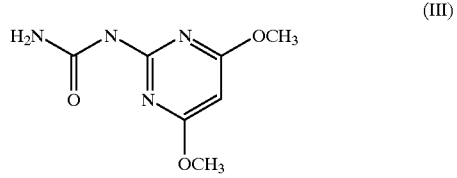

(III)

are new, have been especially developed for the process according to the invention, and therefore constitute a subject of the present invention.

The compounds of formula I or the corresponding sulfonylureas are known and described, for example, in EP-A-0 459 949, EP-A-0 540 697, EP-A-0 103 543, EP-A-0 600 836, and EP-A-0 521 500. The sulfonylurea salts of formula I may be present in amorphous form and as solvates, for example with dioxane, or as hydrates, for example as monohydrates and dihydrates.

The preparation of the starting compound of formula IV is described, for example, in EP-A-0 232 067, page 29. The compounds of formula V may be prepared, for example, by converting the compound of formula VII

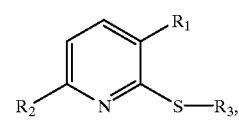

(VII)

wherein $R_1$ and $R_2$ are as defined under formula I and $R_3$ is —$CH_2$-phenyl or isopropyl, to the compound of formula VI through aqueous chlorination. This compound is treated with ammonia, and the resulting sulfonamide is then reacted with 30% sodium methylate. Such reactions are known, and are familiar to the specialist.

The following examples further illustrate the process according to the invention.

PREPARATIVE EXAMPLES

Example H1

Preparation of N-[3-(2-trifluoroethoxy)pyridin-2-yl-sulfonyl]-N'-(4,6-dimethoxypyrimidin-2-yl)urea sodium salt:

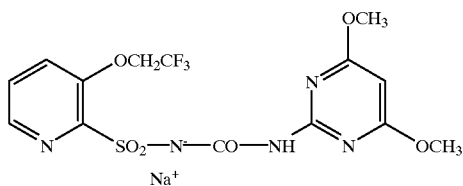

A solution of 23.3 g (0.129 mol) 4,6-dimethoxypyrimidin-2-isocyanate in 720 g dioxane is added dropwise to a suspension of 35.9 g (0.129 mol) 3-(2-trifluorethoxy)pyridin-2-yl-sulfonamide sodium salt in 200 g dioxane over a period of 30 minutes and at a temperature of 50° C. The reaction mixture is then kept for 1 hour at a temperature of 50° C. After cooling, the mixture is filtered through a suction filter, and the residue obtained is washed with 100 g dioxane and then dried at a temperature of 100° C in an oven. 57.16 g of N-[3-(2-trifluoroethoxy)pyridin-2-yl-sulfonyl]-N'-(4,6-dimethoxypyrimidin-2-yl)urea sodium salt is obtained (content: 95%, yield: 92% of theoretical yield).

Comparable results are obtained when the reaction is carried out using tetrahydrofuran as solvent.

Example H2

Preparation of N-[3-(2-trifluoroethoxy)pyridin-2-yl-sulfonyl]-N'-(4,6-dimethoxypyrimidin-2-yl)urea sodium salt:

a) A solution of 23.3 g (0.129 mol) 4,6-dimethoxypyrimidin-2-isocyanate in 560 g dioxane is treated with 3.29 g (0.194mol) $NH_3$ gas for 60 minutes at a temperature of 10 to 15° C.
Concentration of the solution by evaporation yields 27 g 2-aminocarbonylamino-4,6-dimethoxypyrimidine (content: 87 %, yield: 92% of theoretical yield).

b) A solution of 2.2 g (0.01 mol) 2-aminocarbonylamino-4,6-dimethoxypyrimidine in 50 ml tetrahydrofuran is added dropwise to a suspension of 0.87 g (content: 50%, 0.02 mol) sodium hydride in 50 ml tetrahydrofuran after cooling to a temperature of 0 to –5° C. After removal of cooling, allow the temperature to rise to 20° C. and wait until gas evolution has subsided. A solution of 3 g (0.011 mol) 3-(2-trifluoroethoxy)pyridin-2-yl sulfonic chloride in 10 ml tetrahydrofuran is then added dropwise over a period of 10 minutes and the reaction mixture stirred for one hour. At a pressure of 30 kPa and a temperature of 32° C., 60 ml tetrahydrofuran is then distilled until the solution becomes turbid. After removal of the heating bath and stirring of the mixture for 12 hours at a temperature of 20° C., the product crystallises out. The mixture is cooled to a temperature of 0° C. and after 30 minutes filtered through a suction filter. The residue obtained is washed with 15 ml tetrahydrofuran and dried at a temperature of 100° C. 2.8 g of N-[3-(2-trifluoroethoxy)pyridin-2-yl-sulfonyl]-N'-(4,6-dimethoxypyrimidin-2-yl)urea sodium salt is obtained with a content of 97% and a yield amounting to 59% of the theoretical yield.

Using the process according to the present invention, it is possible to prepare N-pyridyl-sulfonyl-N'-pyrimidinylurea sodium and potassium salts in a simple manner and with high yields. By comparison with the salts obtained using the known processes, the sulfonylurea salt prepared according to the present invention unexpectedly possesses a substantially more pronounced crystalline structure and can therefore be separated from the reaction mixture simply and at a markedly faster rate. Moreover, especially in the reaction of a compound of formula IV with a compound of formula V, surprisingly high yields are achieved amounting to more than 90% of theoretical yield in a reaction of up to 99.5%, which is not possible with the known processes.

What is claimed is:

1. A process for the preparation of a compound of formula I

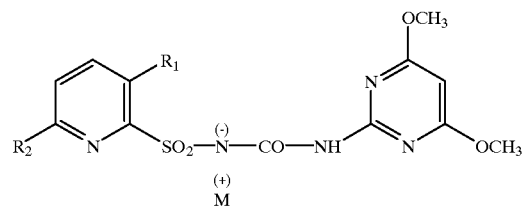

wherein $R_1$ is selected from the group consisting of —$CO_2CH_3$, —$CON(CH_3)_2$, —$OCH_2CF_3$, —$N(CH_3)COCH_3$, —$N(CH_3)SO_2CH_3$, —$CF_3$, and —$SO_2C_2H_5$;

$R_2$ is selected from the group consisting of hydrogen and —$CF_3$; and

M is selected from the group consisting of sodium and potassium;

comprising:
reacting a compound of formula IV

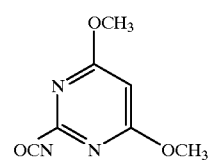

in an aprotic, organic solvent with a compound of formula V

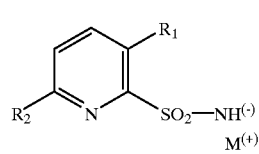

wherein $R_1$, $R_2$, and M are as defined above.

2. The process of claim 1 wherein $R_1$ is —$OCH_2CF_3$ and $R_2$ is hydrogen.

3. The process of claim 1 wherein M is sodium.

4. The process of claim 1 wherein 3-(2-trifluoroethoxy)pyridin-2-ylsulfonamide sodium salt is reacted with 4,6-dimethoxypyrimidin-2-isocyanate at a temperature of 30 to 80° C. in a solvent selected from the group consisting of dioxane and tetrahydrofuran.

* * * * *